(12) United States Patent
Ament

(10) Patent No.: US 8,906,297 B1
(45) Date of Patent: Dec. 9, 2014

(54) TOOTHBRUSH SANITIZER

(76) Inventor: Christine Ament, Cypress, CA (US)

( * ) Notice: Subject to any disclaimer, the term of this patent is extended or adjusted under 35 U.S.C. 154(b) by 897 days.

(21) Appl. No.: 13/093,922

(22) Filed: Apr. 26, 2011

(51) Int. Cl.
*A61L 2/08* (2006.01)
*A61L 2/00* (2006.01)
*A61L 9/00* (2006.01)

(52) U.S. Cl.
USPC .............................. 422/26; 422/292; 422/300

(58) Field of Classification Search
CPC .......... A46B 17/00; A46B 17/06; A47K 1/09; A61L 2/00; A61L 2/02; A61L 2/04; A61L 2/07; A61L 2/26; A61L 2202/122; A61L 2202/24
USPC ............................................ 422/26, 292, 300
See application file for complete search history.

(56) References Cited

U.S. PATENT DOCUMENTS

| | | |
|---|---|---|
| 5,023,460 A | 6/1991 | Foster, Jr. et al. |
| 5,253,927 A | 10/1993 | Erickson |
| 5,882,613 A | 3/1999 | Gipson, II |
| D413,986 S | 9/1999 | Lin |
| D542,929 S | 5/2007 | Shin |
| 7,213,603 B2 | 5/2007 | Pinsky |
| 2004/0033182 A1 | 2/2004 | Duffy |
| 2006/0029518 A1* | 2/2006 | Yu .................................. 422/62 |

FOREIGN PATENT DOCUMENTS

| | | | |
|---|---|---|---|
| DE | 20113556 | * | 11/2001 |
| JP | 2002336052 | * | 11/2002 |

OTHER PUBLICATIONS

Machine translation of JP2002336052 provided by esp@cenet, retreived Aug. 20, 2014.*

* cited by examiner

*Primary Examiner* — Christopher K Vandeusen
(74) *Attorney, Agent, or Firm* — Kyle A. Fletcher, Esq.

(57) ABSTRACT

The toothbrush sanitizer is a small device that can sanitize the head of a toothbrush, and includes a small steam chamber that is accessibly via sealed opening. The sealed opening is adjacent the small chamber and includes a rubber seal that opens upon entrance of a toothbrush head therein. A heating element is positioned between a water reservoir and the small chamber. The heating element is responsible for forming steam and directing said steam onto the toothbrush head located in the small steam chamber. The toothbrush sanitizer is powered by batteries or includes an electrical plug that extends from a rear surface to plug the device into an electrical outlet.

14 Claims, 5 Drawing Sheets

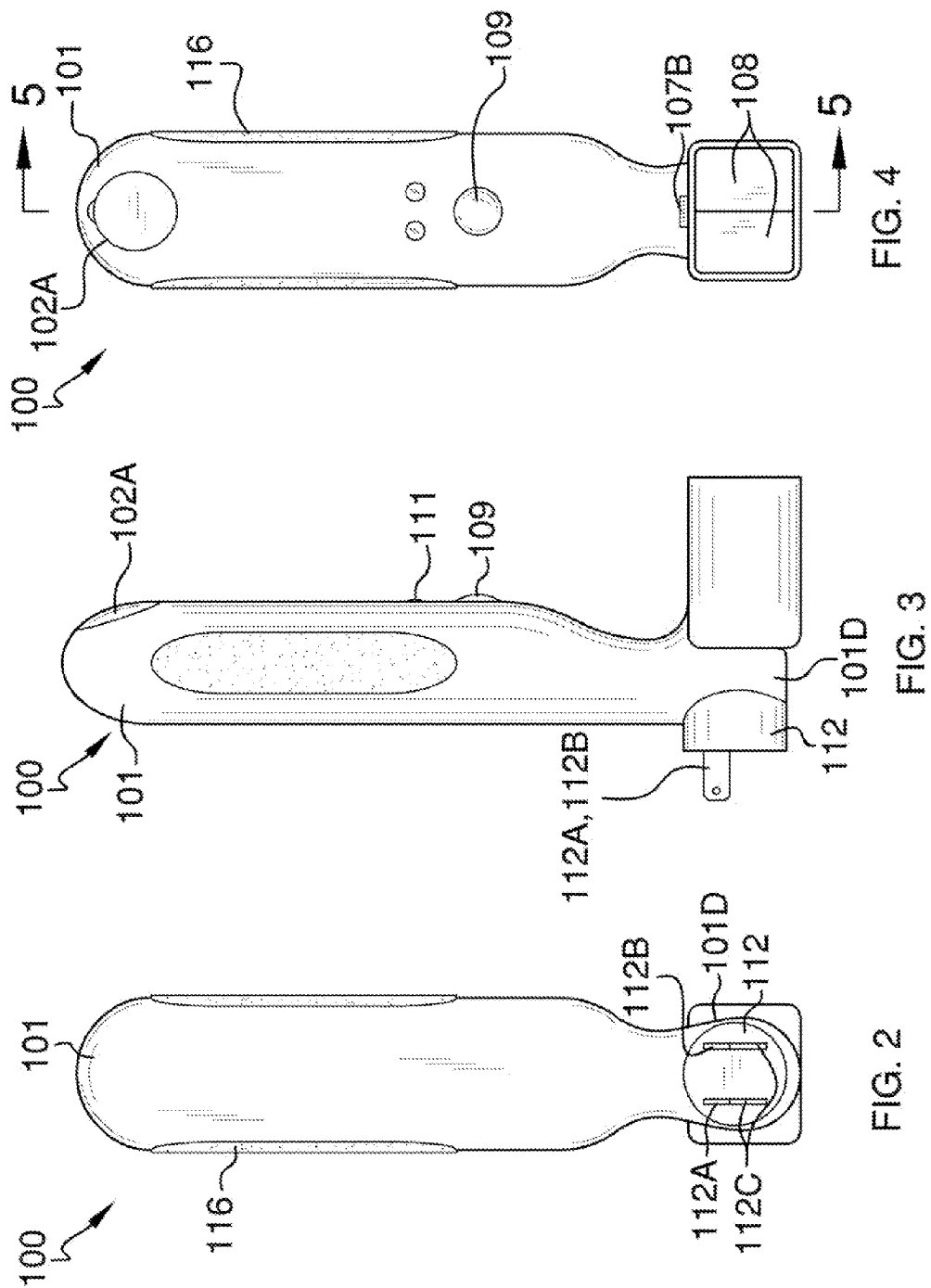

TOOTHBRUSH SANITIZER

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

A. Field of the Invention

The present invention relates to the field of toothbrushes, more specifically, a portable toothbrush sanitizer.

B. Discussion of the Prior Art

As will be discussed immediately below, no prior art discloses a toothbrush sanitizer that plugs into a standard wall outlet and of which has a small reservoir filled with water and a heating element that forms steam that is directed onto a toothbrush head located inside of a sealed entry; wherein the toothbrush sanitizer is small and highly portable; wherein the toothbrush sanitizer features a collapsible electrical plug that can fold out for insertion into an electrical outlet or alternatively employs the use of batteries to form steam; wherein the toothbrush sanitizer includes a small chamber accessible from a sealed entry and of which enables entrance of a head of a toothbrush therein to sanitize via steam.

The Yu Patent Application Publication (U.S. Pub. No. 2006/0029518) discloses a toothbrush sterilizer and cleaner including a steam chamber and a temperature control switch. However, the sterilizer does not teach a steaming chamber in fluid connection with an inlet and upon which only the head of the toothbrush is inserted through a sealed opening at said inlet in order to engage steam upon the head of the toothbrush.

The Duffy Patent Application Publication (U.S. Pub. No. 2004/0033182) discloses an oral hygiene device sanitizer having a water chamber positioned adjacent to a controllable heater to generate steam to be mixed with heated air for sanitization. Again, the sanitizer includes a chamber that is large enough to enclose an entire toothbrush and not a small chamber into which a head of a toothbrush is inserted and steamed directly.

The Erickson Patent (U.S. Pat. No. 5,253,927) discloses a toothbrush recycling apparatus and method that includes a heater for heating water in the chamber to produce steam. However, the apparatus is not a portable sanitizer that projects steam onto a head of a toothbrush.

The Gipson, II Patent (U.S. Pat. No. 5,882,613) discloses a toothbrush holder and sanitizer flush apparatus. Again, the sanitizer is not directed to sanitizing only the head of the toothbrush, and does not teach an inlet that is sealed by a rubber seal and through which the head of a toothbrush is inserted into.

The Pinsky Patent (U.S. Pat. No. 7,213,603) discloses a system and method for toothbrush sanitization and storage. However, the device has a plurality of apertures and not a single chamber into which only the head of a toothbrush is inserted in order to sterilizer the head of the toothbrush.

The Foster, Jr. Patent (U.S. Pat. No. 5,023,460) discloses a toothbrush sanitizer that has a housing containing a centrally located elongated ultraviolet bulb surrounded by cavities for receiving standing toothbrushes. Again, the sanitizer encases the entire toothbrush and not a small chamber having a sealed opening into which only the head of the toothbrush is inserted.

The Shin Patent (U.S. Pat. No. Des. 542,929) illustrates an ornamental design for a toothbrush sterilizer, which does not teach a chamber into which a toothbrush head is inserted.

The Lin Patent (U.S. Pat. No. Des. 413,986) illustrates an ornamental design for a container for sterilizing toothbrush by steam, which does not teach a chamber into which a toothbrush head is inserted.

While the above-described devices fulfill their respective and particular objects and requirements, they do not describe a toothbrush sanitizer that plugs into a standard wall outlet and of which has a small reservoir filled with water and a heating element that forms steam that is directed onto a toothbrush head located inside of a sealed entry; wherein the toothbrush sanitizer is small and highly portable; wherein the toothbrush sanitizer features a collapsible electrical plug that can fold out for insertion into an electrical outlet or alternatively employs the use of batteries to form steam; wherein the toothbrush sanitizer includes a small chamber accessible from a sealed entry and of which enables entrance of a head of a toothbrush therein to sanitize via steam. In this regard, the toothbrush sanitizer departs from the conventional concepts and designs of the prior art.

SUMMARY OF THE INVENTION

The toothbrush sanitizer is a small device that can sanitize the head of a toothbrush, and includes a small steam chamber that is accessibly via sealed opening. The sealed opening is adjacent the small chamber and includes a rubber seal that opens upon entrance of a toothbrush head therein. A heating element is positioned between a water reservoir and the small chamber. The heating element is responsible for forming steam and directing said steam onto the toothbrush head located in the small steam chamber. The toothbrush sanitizer is powered by batteries or includes an electrical plug that extends from a rear surface to plug the device into an electrical outlet.

An object of the invention is to provide a portable toothbrush sanitizer that can sanitize only the head of a toothbrush via a small sanitizer chamber.

A further object of the invention is to provide a sealed opening adjacent the small sanitizer chamber, which seals off the exterior from the small sanitizer chamber.

A further object of the invention is to provide a toothbrush sanitizer that includes a small sanitizer chamber hingedly engaged upon a housing containing both a heating element and a water reservoir.

A further object of the invention is to provide a powering means for the toothbrush sanitizer that comprises at least one battery or an electrical plug that is rotatable engaged from a rear surface of the housing.

These together with additional objects, features and advantages of the toothbrush sanitizer will be readily apparent to those of ordinary skill in the art upon reading the following detailed description of presently preferred, but nonetheless illustrative, embodiments of the toothbrush sanitizer when taken in conjunction with the accompanying drawings.

In this respect, before explaining the current embodiments of the toothbrush sanitizer in detail, it is to be understood that the toothbrush sanitizer is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the toothbrush sanitizer.

It is therefore important that the claims be regarded as including such equivalent construction insofar as they do not depart from the spirit and scope of the toothbrush sanitizer. It is also to be understood that the phraseology and terminology employed herein are for purposes of description and should not be regarded as limiting.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention:

In the drawings:

FIG. 2 illustrates a back view of the housing and the electrical plug;

FIG. 3 illustrates a side view of the toothbrush sanitizer;

FIG. 4 illustrates a front view of the toothbrush sanitizer;

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Detailed reference will now be made to the preferred embodiment of the present invention, examples of which are illustrated in FIGS. 1-6. A toothbrush sanitizer 100 (hereinafter invention) includes a housing 101 that is responsible for containing a reservoir 102 at a top end 101A of the housing 101. The reservoir 102 has an inlet 102A that enables access to the reservoir 102. The inlet 102A is located on the top end 101A of the housing 101 and rotates about a hinge 102B.

Figure 1:
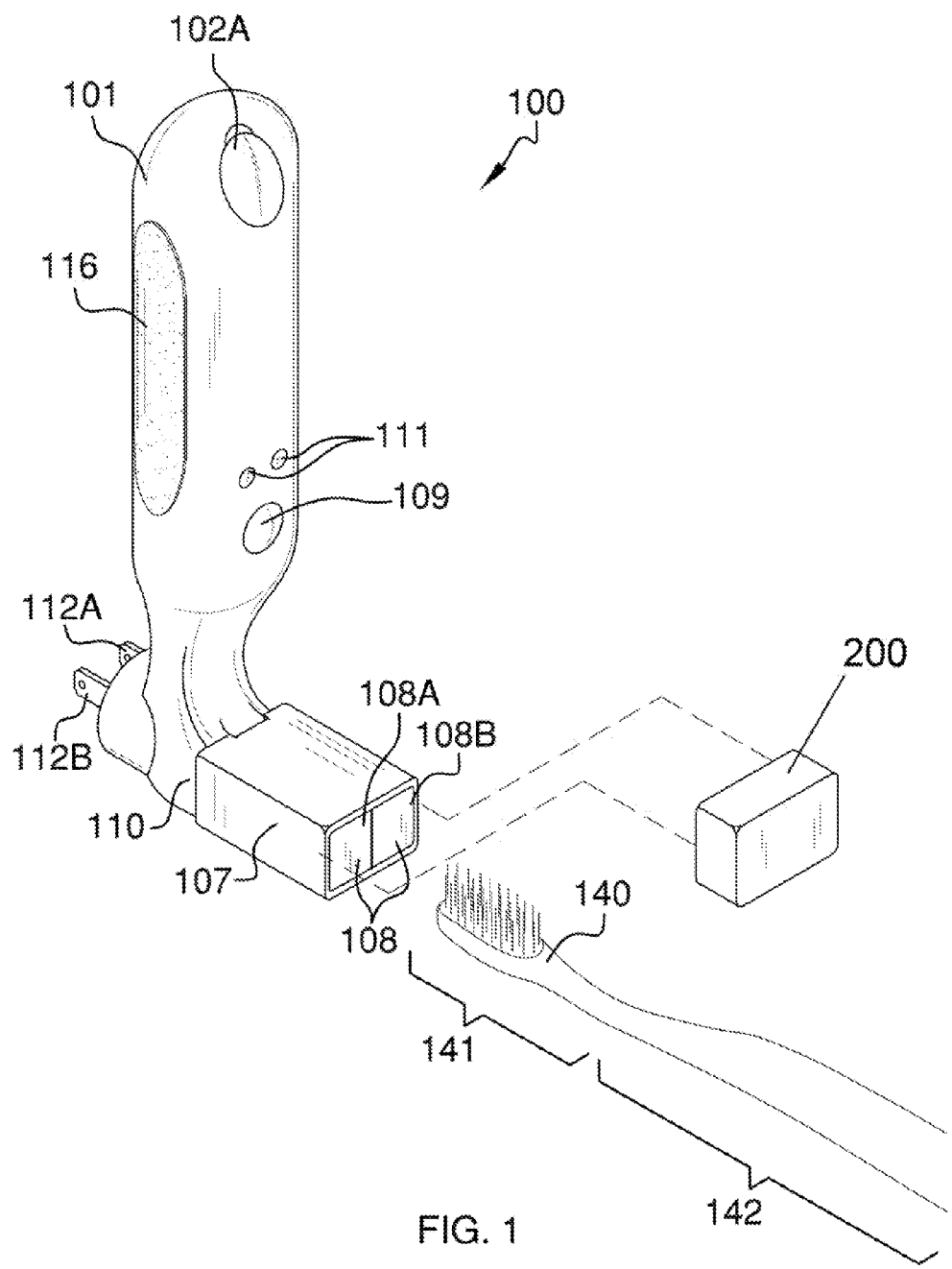
FIG. 1 illustrates a front, perspective view of the toothbrush sanitizer and a toothbrush head aligned adjacent the rubber seal and a removable cap removed from the steam chamber.
Figure 6:
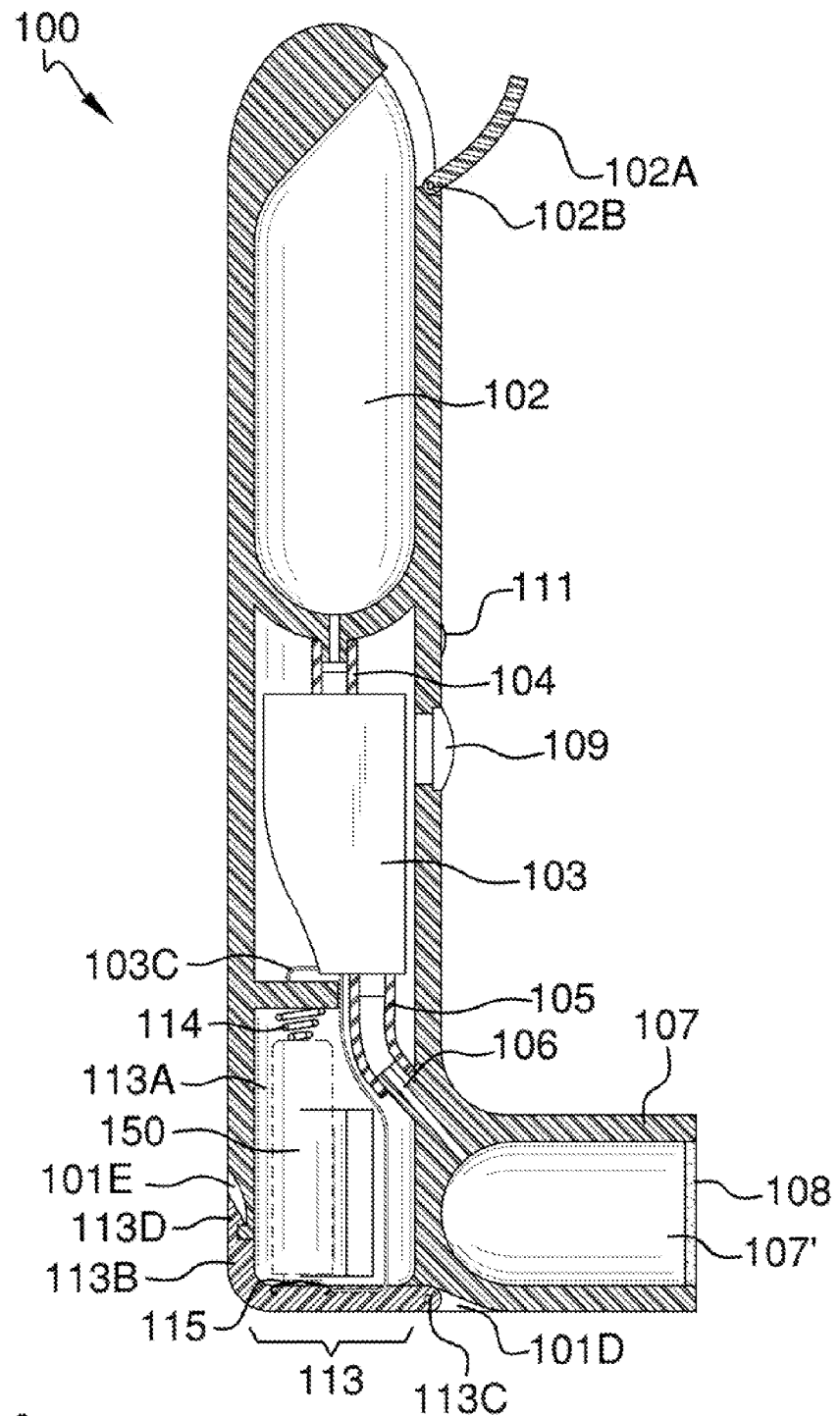
FIG. 6 illustrates the cross-sectional view of FIG. 5 and depicting the inclusion of a battery compartment inside of the housing in place of the electrical plug.

Referring to FIGS. 1 and 6, the inlet 102A forms a funnel-shape when opened to aid in the introduction of water 130.

The reservoir 102 includes an outlet 102C, which is located at a bottom of the reservoir 102. The outlet 102C is in fluid communication with a heating element 103 via an inlet tube 104. The heating element 103 is in fluid communication with the inlet tube 104 via an inlet 103A that is located at a top end of the heating element 103. It shall be noted that the invention 100 relies upon gravity to draw water down from the reservoir 102 and into the heating element 103.

The heating element 103 is responsible for in-taking water 130 fed into the heating element 103, and transforming said water 130 into steam 131. The heating element 103 is encased within the housing 101 in a middle 101B of the housing 101. The steam 131 is dispensed from the heating element 103 through an outlet tube 105. The outlet tube 105 connects to an outlet 103B located at a bottom end of the heating element 103. The outlet tube 105 is in fluid communication with a channel 106. The channel 106 directs steam 131 into a sanitizing chamber 107. The sanitizing chamber 107 is small in size and can accommodate a head 141 of a toothbrush 140. In other words, the sanitizing chamber 107 is a cavity 107' in the shape of a hollow rectangularly-shaped box having an opening of not less than 1 inch by 1 inch, and a length of not less than 2 inches.

The sanitizing chamber 107 is responsible for directing the steam 131 onto the head 141 of the toothbrush 140, which is the entire function behind the use of the invention 100. It shall be noted that the duration of exposure of the toothbrush head 141 to the steam 131 is dependent upon current standards relative to sanitization generally.

The size of the cavity 107' is crucial since the overall volume of the cavity 107' can accommodate the head 141 of the toothbrush 140, and not the entire toothbrush 140. More importantly, the size of the cavity 107' limits the overall size of the invention 100, and makes the overall size and shape of the invention 100 smaller than is normally required.

The sanitizing chamber 107 has an inlet 107A that is in fluid communication with the channel 106. The inlet 107A aligns with the channel 106 to direct steam 131 into the sanitizing chamber 107.

Figure 5:
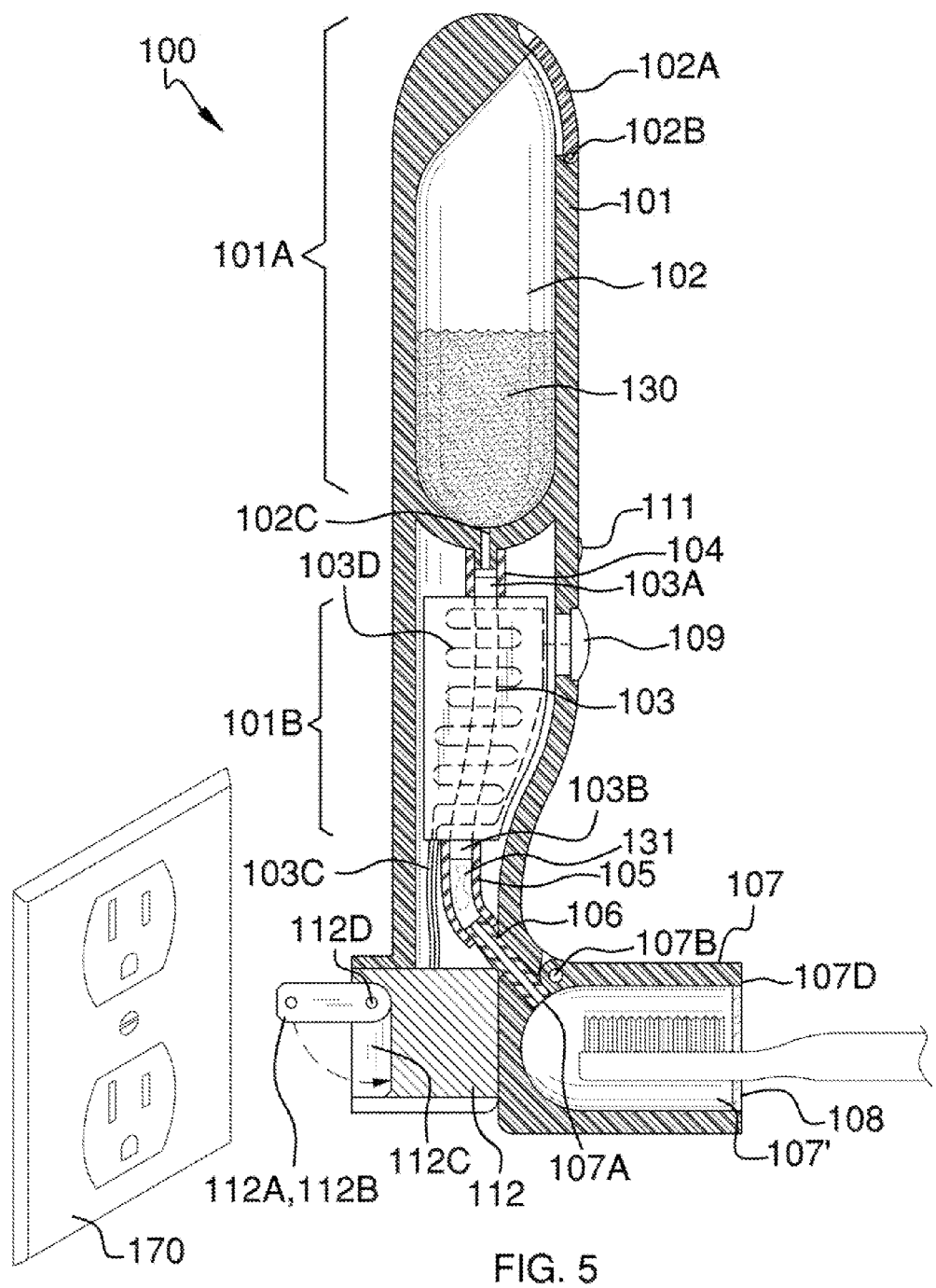
FIG. 5 illustrates a cross-sectional view of the toothbrush sanitizer along line 5-5 in FIG. 4, and defining the spatial relationship of the reservoir, the heating element, wiring, hinge, and small sanitizer chamber, and depicting rotational movement of the electrical plug from the rear of the housing of the toothbrush sanitizer.
Figure 5A:
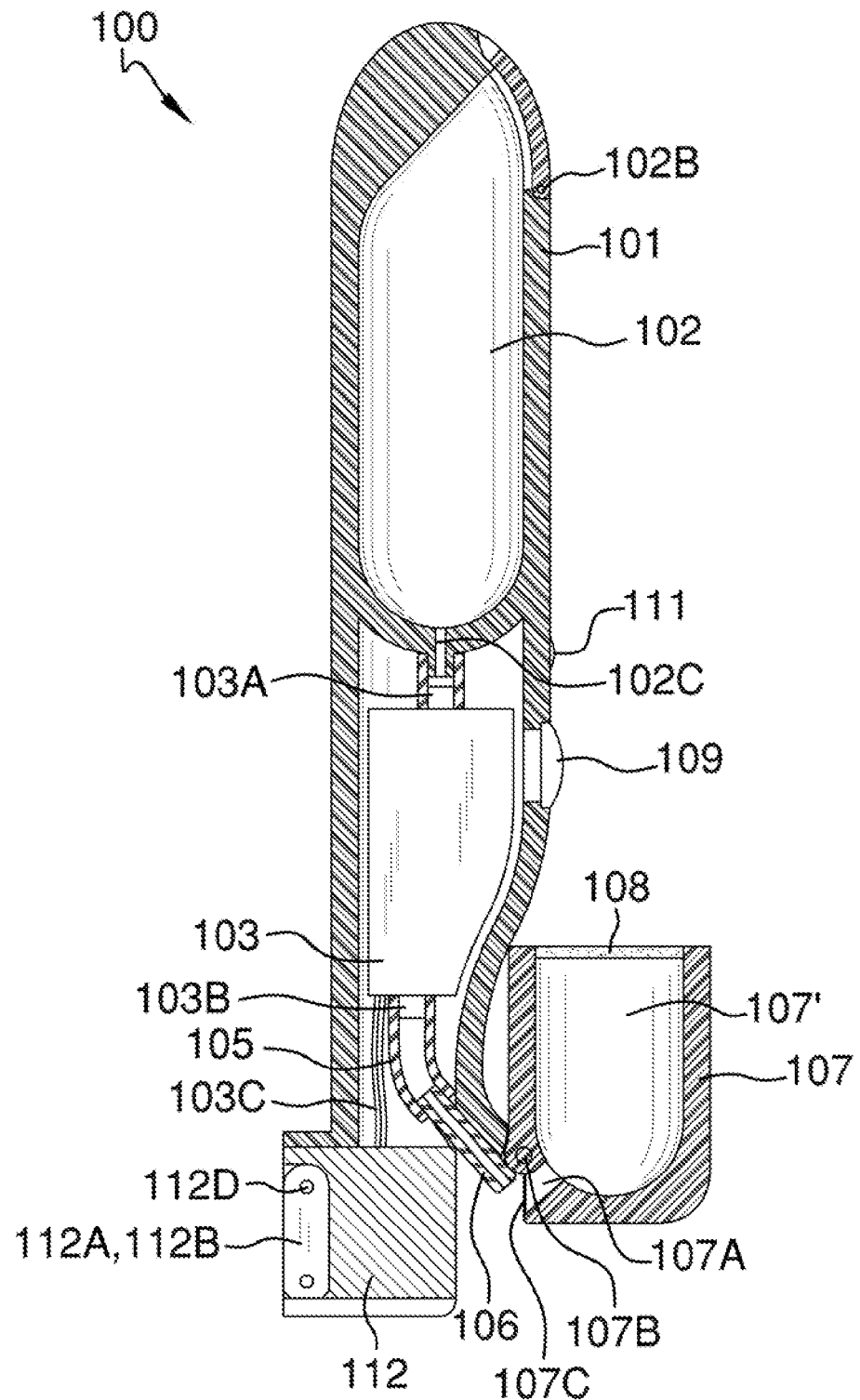
FIG. 5A illustrates the cross-sectional view of FIG. 5, and further detailing the rotation of the small sanitizer chamber with respect to the housing via the hinge, and depicting both the rubber seal at the front inlet as well as a flap seal located on a back inlet.

The sanitizing chamber 107 has a hinge 107B that enables the sanitizing chamber 107 to rotate with respect to the housing 101. The sanitizing chamber 107 is in an extended position when the sanitizing chamber 107 abuts against the housing 101 forming a line 110. The hinge 107B enables the invention 100 to fold up into a retracted position (see FIG. 5A) when not in use. A flap seal 107C rotates down to cover the inlet 107A when the invention 100 is no longer in use (see FIG. 5A). The flap seal 107C is a spring-loaded seal that is made of a material comprising a plastic or rubber that is designed to seal off the inlet 107A when the invention 100 is no longer in use so as to protect the cavity 107' from contamination from outside of the invention 100.

The sanitizing chamber 107 includes a front entrance 107D that is lined with a rubber seal 108. It shall be noted that the front entrance 107D is a square having a size of not less than 1 inch by 1 inch. The rubber seal 108 is composed of a first half 108A and a second half 108B that form a seal that covers the front entrance 107D. A border 108' is formed where the first half 108A and the second half 108B abut one another. An end user would grab the toothbrush 140 by a handle 142, and insert the head 141 of the toothbrush 140 through the rubber seal 108 by separating the first half 108A from the second half 108B at the border 108' (see FIG. 5).

The heating element 103 is wired to an on/off switch 109, which simply turns the heating element 103 on or off and of which when turned on will deliver steam 131 from the heating element 103 through the outlet tube 105 through the channel 106 in the inlet 107A and into the cavity 107' of the sanitizing chamber 107 where the toothbrush head 141 is sanitized via the steam 131.

The heating element 103 is wired to at least one light 111, which is located on the housing 101 and provides feedback to the end user as to the status of the heating element 103. The heating element 103 is connected via a wire 103C to a powering means comprising a collapsible outlet 112 (see FIGS. 5-5A) or at least one battery 150 located in a battery compartment 113 (see FIG. 6). It shall be noted that the heating element 103 employs the use of a known technology for converting water 130 into steam 131, which includes the use of a resistance coil 103D that gets hot when an electrical current is passed through the resistance coil. Water is exposed to the heated resistance coil, conduction occurs, and the water 130 is transformed into steam 131 that exists the outlet 103B.

Referring to FIGS. 1, 3, 5, and 5A, the collapsible outlet 112 is located at a bottom end 101D of the housing 101. More particularly, the collapsible outlet 112 is located on an opposite side of the housing 101 from the sanitizing chamber 107. The collapsible outlet 112 is wired to the heating element 103 and the on/off switch 109. The collapsible outlet 112 includes electrical prongs 112A and 112B that rotate out from a recess 112C formed into a rear surface 112D of the collapsible outlet 112. The electrical prongs 112A and 112B are for use with an electrical outlet, and rotate about a hinge 112D Referring to FIG. 6, an alternative embodiment of the invention 100 includes the battery compartment 113 instead of the collapsible outlet 112. The battery compartment 113 includes a cavity 113A that is accessible from a cover 113B. The cover 113B rotates about a hinge 113C located on the bottom end 101D of the housing 101. A notch 113D located on the cover 113B interacts with a groove 101E located on the housing 101 and enables the cover 113B to close and lock or open and unlock the cover 113B with respect to the housing 101.

The battery compartment 113 includes a first terminal 114 and a second terminal 115 that engage opposing anodes of the battery 150 and of which transmits an electrical current from the battery 150 to the heating element 103.

The only other deviation of the second embodiment of the invention 100 is that the sanitizing chamber 107 does not include the hinge 107B such that the sanitizing chamber 107 is affixed with respect to the housing 101. Accordingly, there is no further use of the flap seal 107C.

The housing 101 may include rubber grips 116 on each side of the housing 101, and provide a means for holding the invention 100 when inserting the toothbrush head 141 into the sanitizing chamber 107 or aligning the electrical prongs 112A and 112B into an electrical outlet 170. The housing 101 may be made of a material comprising a plastic, carbon fiber composite, or a metal. The overall size of the housing 101 and that of the invention 100 shall be no longer than 8 inches. The housing 101 needs to be relatively small and similar in size to maybe a tube of toothpaste such that the invention 100 is relatively small enough for travelers to take or as an applicant that does not take up much space in and around a bathroom.

Referring to FIG. 1, a removable cap 200 is provided and of which is placed around the frontward portion of the sanitizing chamber 107 when not in use. The removable cap 200 prevents germs and/or bacteria from encountering the rubber seal 108. The removable cap 200 insures the overall effectiveness of the invention 100 is not minimized with keeping clean the rubber seal 108 before and after use.

With respect to the above description, it is to be realized that the optimum dimensional relationship for the various components of the invention 100, to include variations in size, materials, shape, form, function, and the manner of operation, assembly and use, are deemed readily apparent and obvious to one skilled in the art, and all equivalent relationships to those illustrated in the drawings and described in the specification are intended to be encompassed by the invention 100.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A toothbrush sanitizer, further comprising:
   a reservoir in fluid communication with a heating element, which is in fluid communication with a sanitizing chamber that can only accommodate a head of a toothbrush;
   wherein water is transformed from water to steam via the heating element and said steam is directed into the sanitizing chamber and onto the head of the toothbrush;
   wherein the reservoir and heating element are both disposed within a housing;
   wherein the heating element includes an outlet that dispels steam through an outlet tube that is in fluid communication with the outlet;
   wherein the outlet tube is in fluid communication with a channel;
   wherein the channel is in fluid communication with the sanitizing chamber;
   wherein the sanitizing chamber includes a steam inlet that is in fluid communication with the channel and which directs steam down from the heating element and into the sanitizing chamber;
   wherein the sanitizing chamber is hingedly attached to the housing and can rotate to an extended or retracted position;
   wherein a flap seal rotates down to cover the steam inlet when the sanitizing chamber is rotated to the retracted position and no longer in use.

2. The toothbrush sanitizer as described in claim 1 wherein the reservoir is located above the heating element such that gravity will draw water contained within the reservoir down into the heating element.

3. The toothbrush sanitizer as described in claim 2 wherein the reservoir has an inlet that is located on a top end of the housing; wherein the inlet includes a hinge that enables the inlet to provide access to the reservoir.

4. The toothbrush sanitizer as described in claim 2 wherein the reservoir includes an outlet located at a bottom of the reservoir; wherein the outlet is in fluid communication with the heating element via an inlet tube; wherein the inlet tube that is in fluid communication with an inlet located at a top of the heating element.

5. The toothbrush sanitizer as described in claim 1 wherein the sanitizing chamber has a cavity in the shape of a hollowed rectangular box having an opening of not less than 1 inch by 1 inch, and a length of not less than 2 inches.

6. The toothbrush sanitizer as described in claim 1 wherein the sanitizing chamber includes a front entrance that includes a rubber seal that is composed of a first half and a second half that form a seal that covers the front entrance; wherein a border is formed where the first half and the second half abut one another; whereupon insertion of the head of the toothbrush through the rubber seal by separating the first half from the second half at the border; a removable cap is provided and of which is placed around the front entrance of the sanitizing chamber when not in use so as to protect the rubber seal from exposure to germs and/or bacteria between uses.

7. The toothbrush sanitizer as described in claim 1 wherein the heating element is wired to an on/off switch, which simply turns the heating element on or off and of which when turned on will deliver steam from the heating element through the outlet tube through the channel and into a cavity of the sanitizing chamber where the toothbrush head is sanitized via the steam; wherein the heating element is connected via a wire to a powering means comprising a collapsible outlet or at least one battery located in a battery compartment; wherein the heating element includes a resistance coil that when heated will heat water to steam.

8. The toothbrush sanitizer as described in claim 7 wherein the collapsible outlet is included where the sanitizing chamber includes a hinge and can rotate with respect to the housing.

9. The toothbrush sanitizer as described in claim 8 wherein the collapsible outlet is located on an opposite side of the housing from the sanitizing chamber; wherein the collapsible outlet includes electrical prongs that rotate out from a recess formed into a rear surface of the collapsible outlet; wherein the electrical prongs rotate about a hinge to an extended state when in use with an electrical outlet.

10. A toothbrush sanitizer, further comprising:
- a reservoir in fluid communication with a heating element, which is in fluid communication with a sanitizing chamber that can only accommodate a head of a toothbrush;
- wherein water is transformed from water to steam via the heating element and said steam is directed into the sanitizing chamber;
- wherein the reservoir is located above the heating element such that gravity will draw water contained within the reservoir down into the heating element and onto the head of the toothbrush
- wherein the reservoir and heating element are both disposed within a housing;
- wherein the heating element includes an outlet that dispels steam through an outlet tube that is in fluid communication with the outlet;

wherein the outlet tube is in fluid communication with a channel;

wherein the channel is in fluid communication with the sanitizing chamber;

wherein the sanitizing chamber includes a steam inlet that is in fluid communication with the channel and which directs steam down from the heating element and into the sanitizing chamber;

wherein the sanitizing chamber is hingedly attached to the housing and can rotate to an extended or retracted position;
- wherein a flap seal rotates down to cover the steam inlet when the sanitizing chamber is rotated to the retracted position and no longer in use.

11. The toothbrush sanitizer as described in claim 10 wherein the reservoir has an inlet that is located on a top end of the housing; wherein the inlet includes a hinge that enables the inlet to provide access to the reservoir; wherein the heating element is wired to an on/off switch, which simply turns the heating element on or off and of which when turned on will deliver steam from the heating element through the outlet tube through the channel and into a cavity of the sanitizing chamber where the toothbrush head is sanitized via the steam; wherein the heating element is connected via a wire to a powering means comprising a collapsible outlet or at least one battery located in a battery compartment.

12. The toothbrush sanitizer as described in claim 11 wherein the sanitizing chamber has a cavity in the shape of a hollowed rectangular box having an opening of not less than 1 inch by 1 inch, and a length of not less than 2 inches.

13. The toothbrush sanitizer as described in claim 11 wherein the sanitizing chamber includes a front entrance that includes a rubber seal that is composed of a first half and a second half that form a seal that covers the front entrance; wherein a border is formed where the first half and the second half abut one another; whereupon insertion of the head of the toothbrush through the rubber seal by separating the first half from the second half at the border; a removable cap is provided and of which is placed around the front entrance of the sanitizing chamber when not in use so as to protect the rubber seal from exposure to germs and/or bacteria between uses.

14. The toothbrush sanitizer as described in claim 11 wherein the collapsible outlet is included where the sanitizing chamber includes a hinge and can rotate with respect to the housing; wherein the collapsible outlet is located on an opposite side of the housing from the sanitizing chamber; wherein the collapsible outlet includes electrical prongs that rotate out from a recess formed into a rear surface of the collapsible outlet; wherein the electrical prongs rotate about a hinge to an extended state when in use with an electrical outlet.

\* \* \* \* \*